United States Patent [19]
Stevens et al.

[11] Patent Number: 6,063,636
[45] Date of Patent: May 16, 2000

[54] METHOD FOR DETECTING AND DIAGNOSING DISEASE CAUSED BY PATHOLOGICAL PROTEIN AGGREGATION

[75] Inventors: Fred J. Stevens, Naperville; Elizabeth A. Myatt, Riverside, both of Ill.; Alan Solomon, Knoxville, Tenn.

[73] Assignees: The United States of America as represented by the United States Department of Energy, Washington, D.C.; The University of Tennessee, Knoxville, Tenn.

[21] Appl. No.: 08/605,294

[22] Filed: Jan. 19, 1996

Related U.S. Application Data

[62] Division of application No. 08/282,473, Jul. 29, 1994, abandoned.

[51] Int. Cl.$^7$ .................................................. G01N 30/02
[52] U.S. Cl. ............................ 436/86; 436/64; 436/161; 530/412; 530/417
[58] Field of Search .................................... 436/161, 512, 436/514, 515, 64, 86; 210/656; 530/412, 417

[56] References Cited

U.S. PATENT DOCUMENTS 4,762,617  8/1988  Stevens .................................... 210/635

OTHER PUBLICATIONS

Short et al. J.Chromatogr. vol. 323, No. 2 p 418–23 (1985).
Berggard et al. J. Biol. Chem vol. 244 No. 16 p 4299–307 (1969).

Stevens et al. Proc. Natl. Acad. Sci. USA vol. 77 No. 2 p 1144–8 (1980).

Alan Solomon, Light Chains of Human Immunoglobulins, pp. 101–121, Methods In Enzymology, vol. 116.

Fred J. Stevens et al., Pathogenic Potential Of Human Monoclonal Immunoglobulin Light Chains, Apr. 1994, pp. 3034–3038, Proc. Natl. Acad. Sci. USA.

Fred J. Stevens, Analysis Of Protein–Protein Interaction By Simulation of Small–Zone Size Exclusion Chromatography, pp. 1155–1167, Biophysical Journal, vol. 55.

Fred J. Stevens et al., Macromolecular Interactions: Application of Microcomputer–Controlled, High Speed Size–Exclusion Chromatography, pp. 340 pp. 340–348, Liquid and Gas Chromatography, vol. 4 No. 4.

*Primary Examiner*—Jan Ludlow
*Attorney, Agent, or Firm*—Joy A. Alwan; Thomas G. Anderson; William R. Moser

[57] ABSTRACT

A method is provided for detecting pathological macromolecules in a patient, comprising obtaining body fluid from the patient, pretreating the body fluid, subjecting the pretreated body fluid to size-exclusion chromatography to create an excluded fluid, and analyzing the excluded fluid to detect macromolecules having a predetermined molecular weight. The method also allows for comparing elution spectra with reference spectra of suspect pathologic proteins.

20 Claims, 4 Drawing Sheets

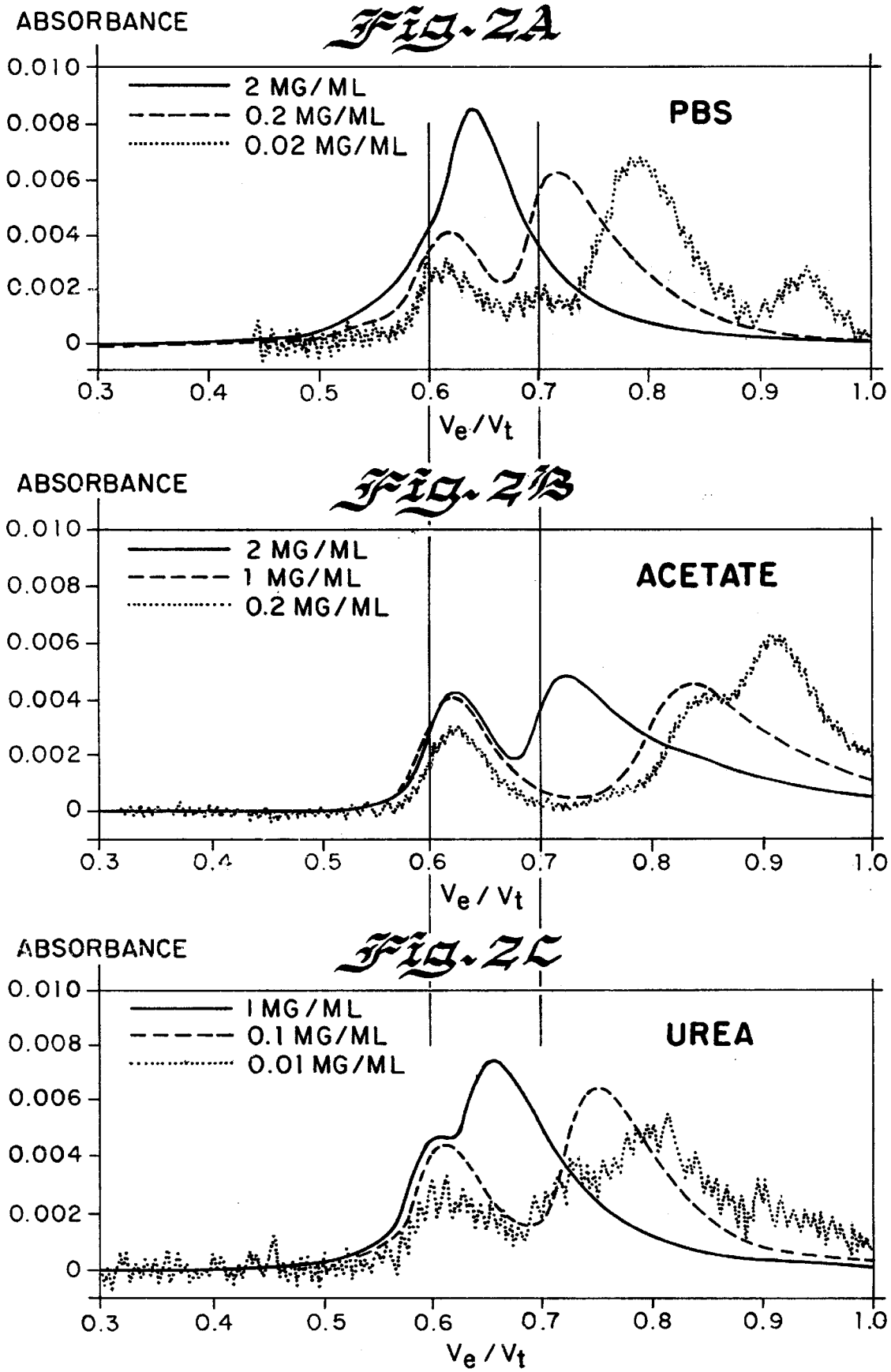

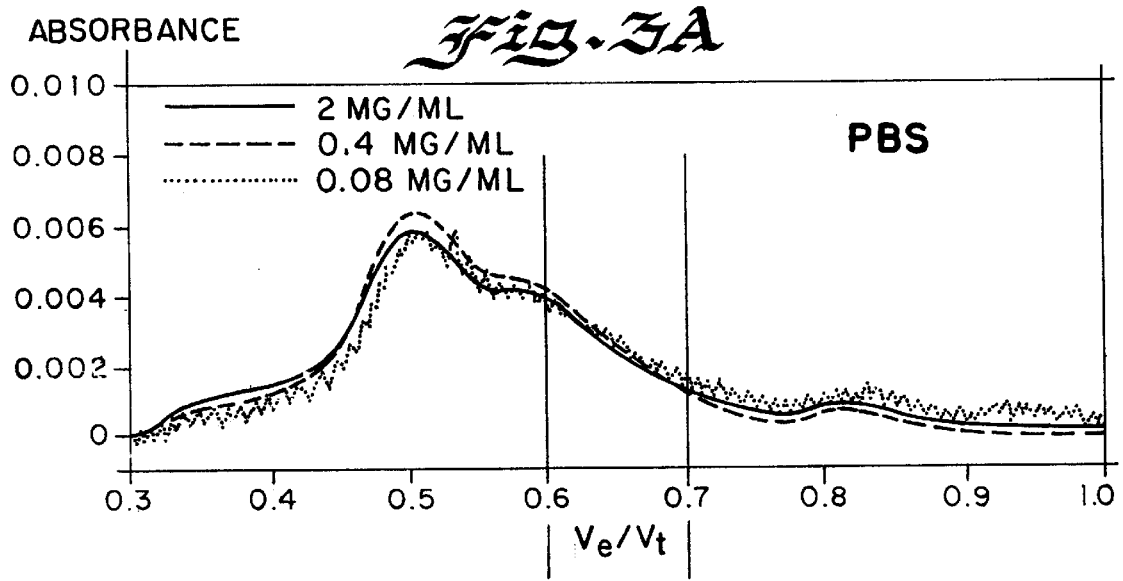
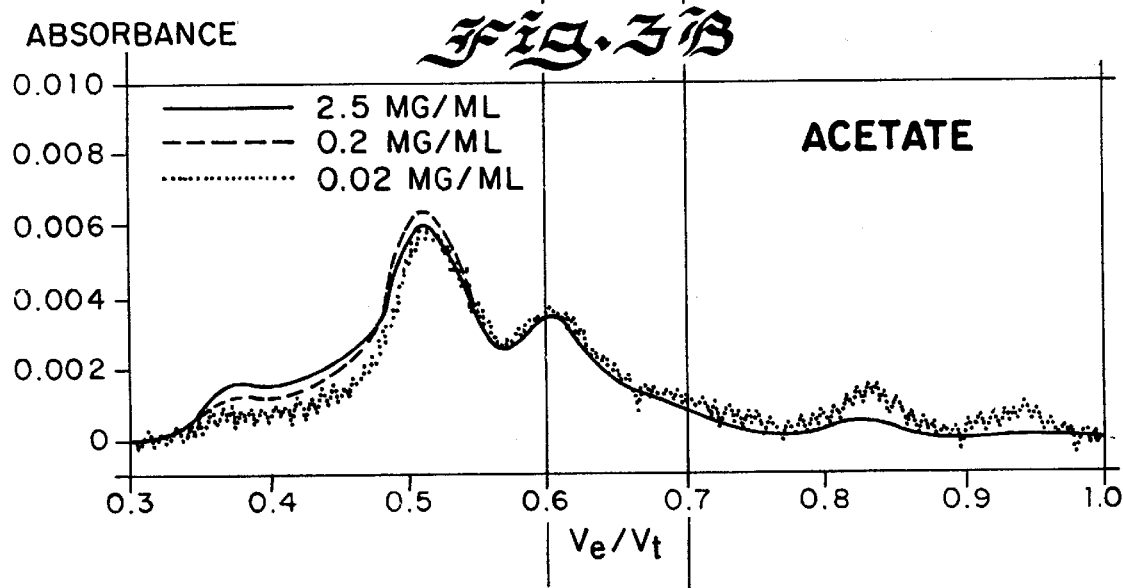
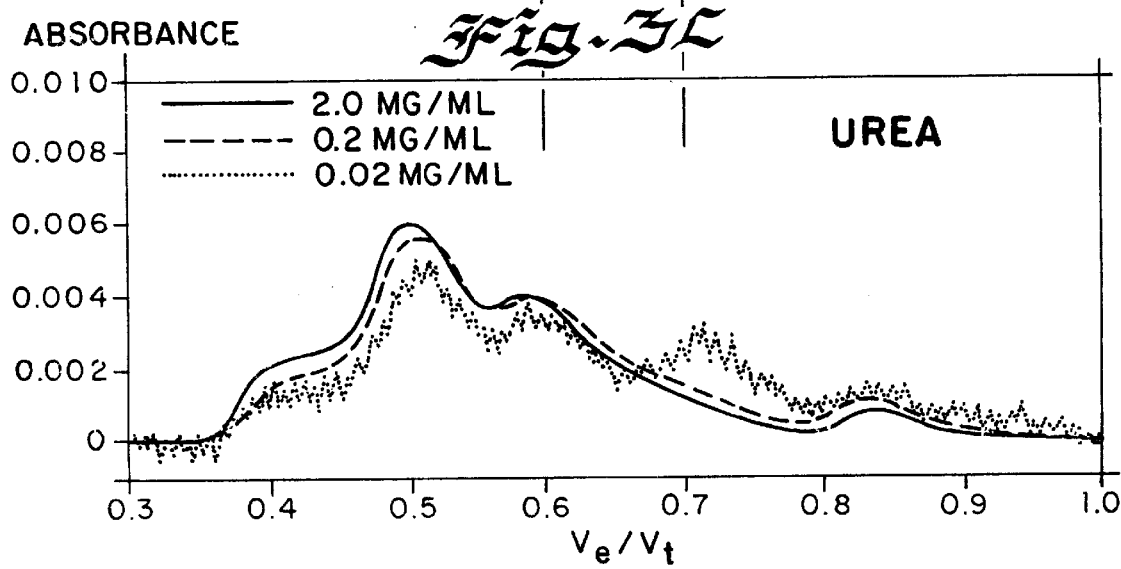

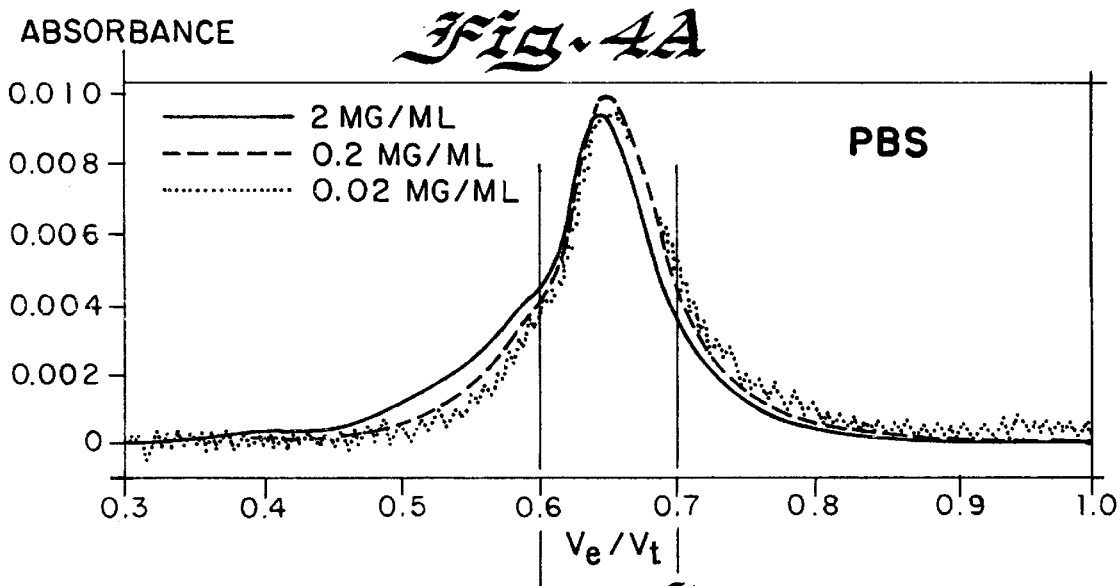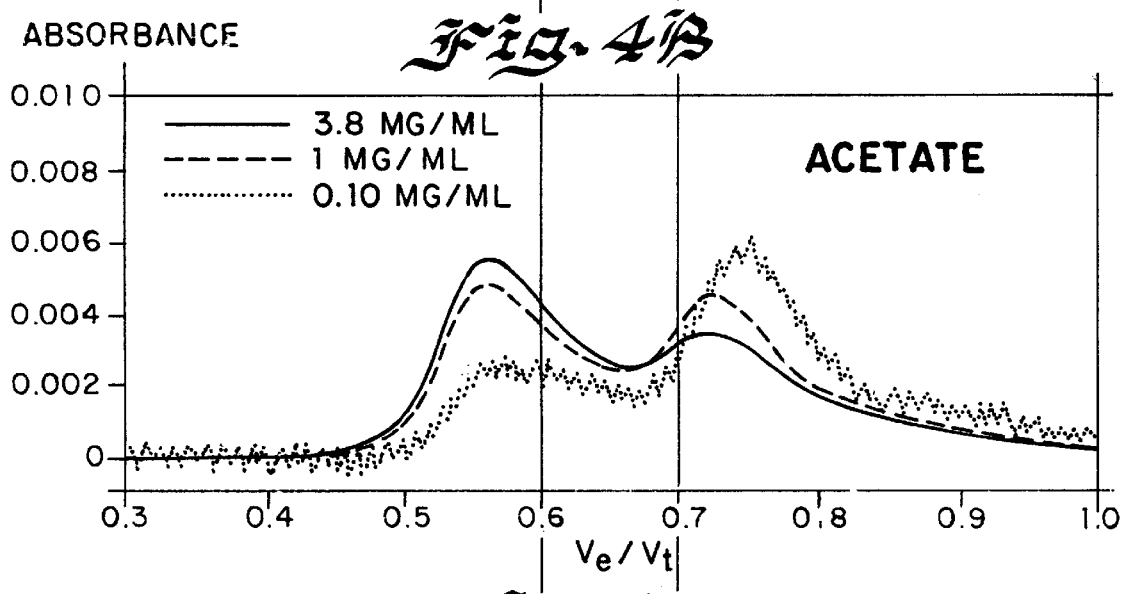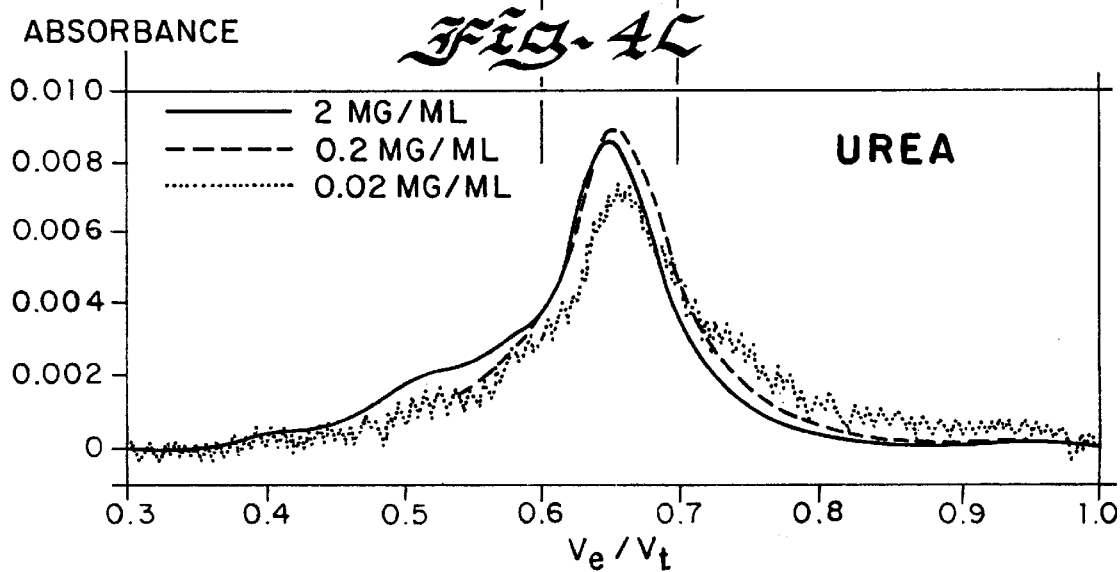

METHOD FOR DETECTING AND DIAGNOSING DISEASE CAUSED BY PATHOLOGICAL PROTEIN AGGREGATION

This is a Division of application Ser. No. 08/282,473 filed Jul. 29, 1994 now abandoned.

CONTRACTUAL ORIGIN OF THE INVENTION

The United States Government has rights in this invention pursuant to Contract No. W-31-109-ENG-38 between the U.S. Department of Energy and The University of Chicago representing Argonne National Laboratory.

BACKGROUND OF THE INVENTION

1. Field of the Invention

This invention relates to a method for detecting pathological macromolecules in body fluids, and more specifically to a method for early detection of pathological, aggregation-specific proteins, the accumulation of which in body tissues leads to organ failure, disease and even death.

2. Background of the Invention

Many diseases affecting organ systems and vessels having extremely narrow passageways are related to the deposition of large macromolecules in those systems and vessels. Susceptible organ systems include the spleen, heart, kidney, liver, lungs, and related vessels.

Renal and systemic diseases of the kidney result from the pathologic deposition of monoclonal antibody light chains, i.e., Bence Jones proteins. Myeloma (cast) nephropathy, light-chain deposition disease, and AL amyloidosis, result from cast formation, basement membrane precipitates, or fibrils, respectively.

Multiple myeloma is a form of cancer principally associated with the elderly. With multiple myeloma, certain cells of the bone marrow become cancerous and multiply, causing production of excessive amounts of a single type of immunoglobulin, which appears in the blood. In such patients, the urine contains large amounts of Bence Jones protein, which is the light chain portion of IgG. Bench Jones protein is found as covalent dimers of light chains, free light chains in monomer/dimer equilibrium, and sometimes as light chain fragments corresponding to either the variable (V) domain or constant (C) domain portions of the protein. These light chains are made in excess of the heavy chains and then excreted. In most cases, the cancerous, dispersed monoclonal proliferation of cells continue to produce antibodies during the disease.

Immunoglobulins are produced by a specialized type of cell known as the B lymphocyte or B cell. A particular B cell and its descendents are known as a clone. In principle, all B cells in a clone are identical and synthesize identical antibodies; i.e., the cells are comprised of identical light chains and identical heavy chains. The antibodies produced by a single clone all have the same physicochemical properties including solubility, stability, and antigen specificity. The natural function of antibodies is to bind to antigens such as bacteria and viruses and thereby enable the body to evoke an immune response and eliminate the pathogen. Because of the large number of potential pathogens, the body has a large number of different B cell clones each of which produces antibodies of different physicochemical properties because the amino acid sequences of the V domains of light and heavy chains are different from those found in other clones.

Multiple myeloma is a cancer that results from the malignancy of a particular clone of B cells. Although the cancer-causing process is unknown, it effectively selects at random a single cell out of potentially hundreds of thousands of choices to generate the malignancy. As a result, although the antibodies produced by a single patient are chemically homogeneous because they are the product of a single clone of cells (monoclonal), the proteins produced by any two patients are different and have different physicochemical properties. It is these differences that leads to different pathological risks for individual patients.

Certain Bence Jones proteins are "malignant" in that they form toxic proteinaceous deposits in the form of renal tubular casts, nonfibrilar basement membrane deposits, and fibrilar amyloid deposits. Aside from the kidney, the latter two types of deposits also may appear in the spleen, heart, other organs or systemically throughout the body. Other Bence Jones proteins are "benign" in that they cause no obvious disease. The "malignant" proteins or their larger products of interaction may block or reduce the function of the organ; as such, the pathology associated with this problem may be considered as a biophysical disease. Death often occurs as a result of this biophysical phenomenon. The ratio of mortality from multiple myeloma in the 70–74 year old age group to that in the 20–24 year old age group is approximately 2000. Between the years 1950 and 1980, the age-corrected mortality rate of multiple myeloma more than doubled. As the population continues to age, the medical significance of multiple myeloma will increase.

Biopsy is one of the few accurate methods used to diagnose protein-deposition disease. However, weak patients often cannot withstand such an invasive procedure for what may turn out to be a bad hunch on the part of attending physicians.

A need exists in the art for a method to rapidly determine the presence of potentially pathological proteins in bodily fluids. There is also a need to diagnose any predisposition for such disease well in advance of its manifestation so that dietary and other medical intervention can be used to stymie subclinical, morphological changes. The method must be accurate, noninvasive and rapid.

SUMMARY OF THE INVENTION

It is an object of the present invention to provide a method to detect the presence of deposit-forming proteins in body fluids that overcomes many of the disadvantages of the prior art.

It is another object of the present invention to provide a method to test for proteins within urine or other body fluid to identify and diagnose any deposit or cast-forming components. A feature of the invention is the use of molecular separation procedures based on size to identify macromolecules associated with protein-aggregation-related disease. An advantage of the invention is enabling physicians to anticipate micro-pathology associated with protein aggregation prior to any manifestation of disease.

Still another object of the present invention is to provide a method to identify potential nephrotoxic or amyloidogenic Bence Jones proteins. A feature of the invention is the utilization of size exclusion chromatography. An advantage of the invention is rapidly obtaining elution profiles from relatively small test samples, thereby leading to rapid and accurate diagnosis.

Yet another object of the present invention is to provide a method to determine under what conditions certain proteins form pathologically significant deposits. A feature of the invention is the use of different buffers to mimic conditions in vivo. An advantage of the invention is enabling treating physicians to implement appropriate therapeutic and dietetic measures to minimize protein deposition.

Another object of the present invention is to provide an in vitro chromatographic system to study the propensity of Bence Jones proteins to aggregate under physiological conditions. A feature of the invention is the use of buffers that reflect pH, osmotic and urea concentration characteristics in the nephron. An advantage of the invention is the ability to detect the presence of malignant Bence Jones proteins via said protein's chromatographically observed properties prior to any manifestation of disease.

Briefly, the above and other objects and advantages of the invention are provided by a method for detecting pathological macromolecules in a patient, comprising obtaining body fluid from the patient, pretreating the body fluid, subjecting the pretreated body fluid to size-exclusion chromatography to create an excluded fluid, and analyzing the excluded fluid to detect macromolecules having a predetermined molecular weight.

The invention also provides for a method to detect aggregated, nephrotoxic antibody light chains in a patient comprising obtaining urine from the patient, isolating protein from the urine, pretreating the protein, subjecting the pretreated protein to size exclusion chromatography so as to create an excluded fluid, subjecting the excluded fluid to ultra violet radiation to observe radiation absorption levels, normalizing the absorption spectra, and comparing the normalized absorption spectra to a database of absorption spectra of nephrotoxic proteins having similar primary structures.

BRIEF DESCRIPTION OF THE DRAWING

These and other objects and advantages of the present invention will become readily apparent upon consideration of the following detailed description and attached drawing, wherein:

FIGS. 3A, 3B and 3C are an elution profile of a toxic protein, in accordance with the features of the present invention;

FIGS. 4A 4B, 4C are an elution profile of another toxic protein, in accordance with the features of the present invention; and FIG. 5 is a graph of three elution profiles comparing toxic and nontoxic proteins, in accordance with the features of the present invention.

DETAILED DESCRIPTION OF THE INVENTION

The pathological expression of excess immunoglobulin light chains in patients with multiple myeloma and amyloidosis is a biophysical phenomenon. Each overproduced light chain, the result of the random selection of its encoding genetic elements, expresses characteristic biophysical properties under physiological conditions which include solubility tendencies, and the kinetics and affinity of self-association and polymerization. The solubility and aggregation of these light chains are determined by their concentration, temperature, pH, ionic strength, ionic composition, and the presence of other molecules that might modulate interaction.

The invented method relates to nephromimitic chromatography for the identification and diagnosis of pathological proteins relating to the kidney or other physiological sites. Specifically, the method is a testing technique to identify and diagnose deposit-forming proteins with particular emphasis on cast-forming monoclonal light chains associated with multiple myeloma.

In order to determine the self-association properties of human light chains, the invented method uses a myriad of techniques to uncover higher-order aggregation of proteins under one or more conditions. Typically, size exclusion chromatography, centrifugation, sedimentation, dialysis, ultrafiltration, density-gradient (zonal) centrifugation, capillary electrophoresis, or standard gel electrophoresis under native conditions can be used to analyze a large number of structurally homologous proteins for aggregation tendencies.

The elution profile of various proteins and their aggregates is determined by their compositional nature, i.e., the presence of covalent or non-covalent dimers, free monomers or light-chain-related fragments, as well as by the formation of higher-order aggregates resulting from solution dependent affinities or other types of interactions. Surprisingly and unexpectedly, it was found that the elution profiles were concentration-dependant, wherein a relative decrease of high-molecular weight components occur following sample dilution, thereby confirming the non-covalent nature of aggregates. This phenomenon demonstrated that the invented in vitro technique could be used to analyze the affinity and kinetic properties of monoclonal light chains.

The invented method is useful in differentiating between pathologic (nephrotoxic and amyloidogenic) and non-pathologic light chains. Pathological molecules having a predetermined weight of approximately 60,000 and 200,000 daltons are detected by the invented method.

Figure 1:
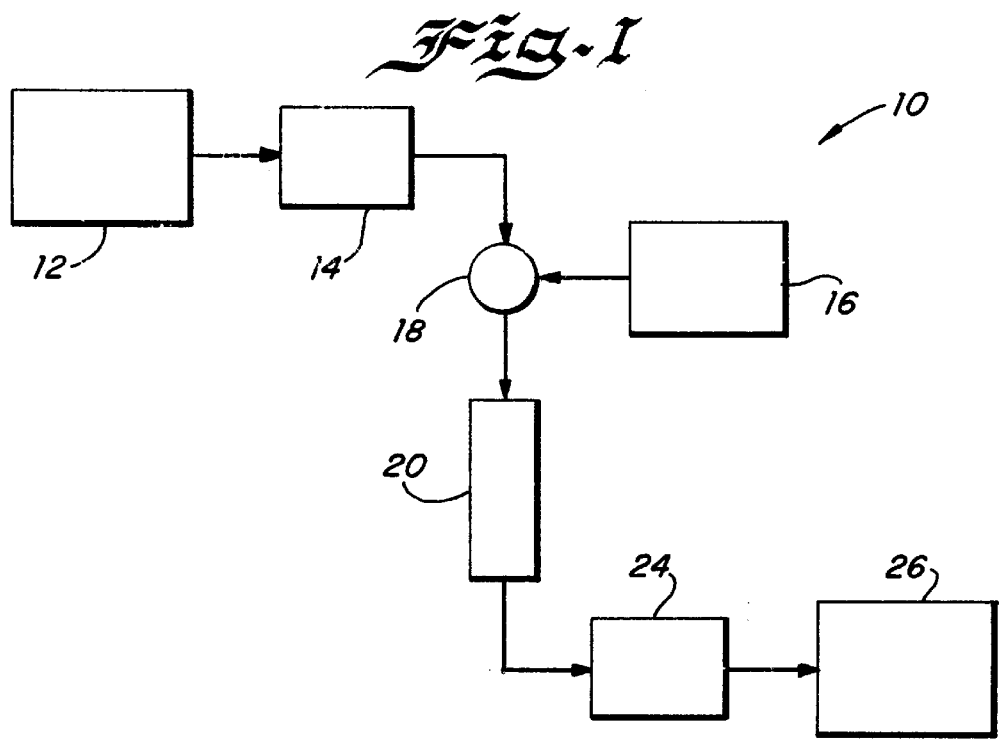
FIG. 1 is a schematic diagram of a method for detecting macromolecules in bodily fluid in accordance with the features of the present invention.
Figure 2:
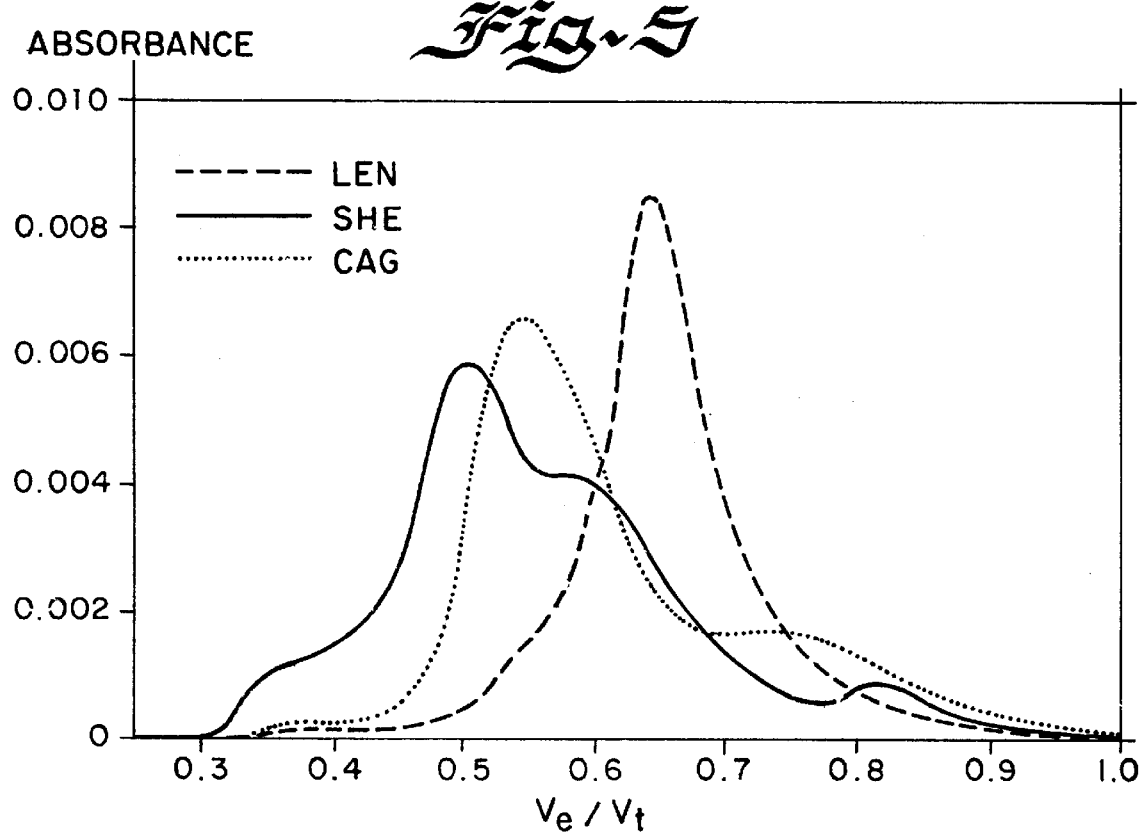
FIGS. 2A, 2B, and 2C are an elution profile of a nontoxic protein, in accordance with the features of the present invention.

Generally, the invented method is depicted in FIG. 1 as item 10, wherein standard size-exclusion chromatography is utilized to separate macromolecules from bodily fluids for subsequent UV-analysis. A more detailed discussion of size-exclusion chromatography, as applied to the study of biological macromolecules, is taught in U.S. Pat. No. 4,762,617, awarded to the applicant, and incorporated herein by reference.

Depending on the protein to be detected or the site of suspected deposition, a predetermined buffer 12, which is selected to mimic the physiological conditions of the deposition site, is supplied to a size-exclusion column 20 at a predetermined flow rate.

The flow rate is determined by a pump 14 situated between the buffer reservoir 12 and the column 20.

After the column is pretreated to block binding sites, which may otherwise withdraw suspect macromolecules from the eluant, the patient-derived sample 16 is supplied to the column 20, via a multi-position valve 18, said valve controlled by a microcomputer, which is not shown. Prior to injection into the column, the patient-derived specimen may be pretreated, such as by subjecting the raw sample to bulk electrophoresis, to remove debris and macromolecules which would confound the characteristic spectra of nephrotoxic proteins. A suitable purification process is described in Solomon, A., (1985) *Methods Enzymol.* 116, 101–121, and incorporated herein by reference.

The resulting excluded volume is then monitored at 214 and 280 nanometers (nm), via a UV-spectrometer 24 and then amplified by an amplifier 26. The two spectra bands are used to enhance detection of protein, with the former band (214 nm) more sensitive to peptides and the later band (280 nm) more sensitive to aromatics, such as phenylalanine, tryptophan and tyrosine.

Size-Exclusion Chromatography Detail

Size-exclusion chromatographic analysis of interacting macromolecules exploits the differences in chromatographic characteristics of the larger complex that is formed by association of the smaller components. Interaction is exhibited by changes in elution behavior that are observed directly without chemical modification of the interacting components.

The invented method is multifaceted in its utility. The technique could be used to generate a protein elution profile to provide guidelines as to the size of proteins being excreted by the patient.

In addition, the technique can be taken a step further with the elution profiles being compared with already determined personality profiles or standard spectra of suspect proteins so as to pinpoint protein types or identity. Standard spectra of a myriad of nephrotoxic proteins, itemized in Table 1, have been produced by the inventor generally by following the procedure outlined in the applicant's recently published paper in *Proc. Natl. Acad. Sci, USA* 91 pp. 3304–3038, April 1994, and incorporated herein by reference.

Determinants of resolution include matrix pore size and column length. Small columns of various lengths and volumes are used to obtain suitable resolutions. A myriad of lengths and volumes have been employed with optimal results. The lengths of the columns could range from approximately 5 cm to 50 cm and the volumes could range from approximately 0.5 ml to 50 ml.

Standard column packing material is used, including but not limited to Superose® (Pharmacia LKB, Piskataway, N.J.), Sephadex® (Pharmacia LKB), and silicone-based resins.

Non-silica-based HPLC matrices offer good pressure tolerances, and depending on the cross section of the column, can withstand flow rates ranging from 0.01 ml/min to 2 ml/min. Faster runs will result in the detection of weak interactions between the light chains, thereby increasing detection levels.

Urinalysis Using Superose

The aggregation propensity of more than 50 different κ- and λ-type Bence Jones proteins were tested under specified conditions of pH, salt and urea concentration that would mimic those found within the nephron.

In the case of urinalysis for Bence-Jones proteins, the following procedure is followed at room temperature: Superose-12® is packed into a 0.3 cm×20- or 25-cm column 20 (Alltech, Deerfield, Ill.). Superose® resin of 10 μm diameter can be obtained in the form of a prepacked column. (Larger size particles of lower resolving capacity are also available at lower cost.) One prepacked Superose® column can yield 10–20 columns of approximately 1–2 ml volume. A hole placed in the end-piece filter allows resin to be pumped from the prepacked column directly into the small receiver column, at a flow rate in excess of that anticipated for routine use. If the HPLC pump is used for this purpose, back pressure can be monitored. Pressure increases as resin accumulates in the small column, with a stabilization of the back pressure indicating that packing is complete. Prior to analytical use, the column is conditioned by passage of several aliquots of protein or serum to block protein-adsorption sites.

Prepared urine specimens 16 are mixed with a chosen buffer 12 at concentrations ranging from between approximately 0.01mg/ml and 50 mg/ml, depending on the sensitivity of the system and the protein being tested. Preferable protein concentrations range from approximately 0.02 to 8.0 mg/ml, and are added to the column in microliter aliquots ranging from 1 μl to 50 μl, and preferably at a volume of 5 μl. An advantage of the invented method is that the dynamic concentration range of the solute (protein) to the solvent (buffer) extends over four orders of magnitude.

Buffers 12 are delivered to the column 20 at approximately 0.06 ml/min using a LKB 2150 pump, 18. Depending on the cross section of the column, 20, buffer flow rates of 0.01 to 2 ml/min can be employed. The excluded volume is then monitored simultaneously at 214 and 280 nm by an HP 1040 multi-scan detector (Hewlett-Packard), 24, during runs of 30 or 35 minutes. The data are collected and stored as described by the applicant in *Biophys. J.* 55, 1155–1167 (1989) and *Liq. Chromatogr. Gas Chromatogr.* 4, 340–348 (1986), and incorporated herein by reference. Chromatographs are normalized by summation of the absorbances at 1000 data points collected during the run and by scaling the data so that the integrated area under the elution profile is equal to one. FIGS. 2–5 represent the elution profiles that are generated. The particular profiles depicted in the figures attached hereto consist of an absorbance scale at 214 nm for the ordinate, and an excluded volume ($V_e$) to total volume ($V_t$) ratio $V_e/V_t$ scale for the abscissa. $V_t$ is determined by measuring the dimensions of the column.

As illustrated in Table 1, many clinically- and/or experimentally-proven nephrotoxic proteins form noncovalent, high molecular weight multimers in vitro.

TABLE 1

Correlation of *in vivo* pathology with *in vitro* aggregation of Bence Jones Proteins.

| Pathology Observed | Protein[1] Type | Aggregation Scores[2] | | |
|---|---|---|---|---|
| | | P[3] | Acetate[3] | Urea[3] |
| None | | | | |
| | Borf (κ) | + | 0 | + |
| | Fin (κ) | 0 | 0 | 0 |
| | Kin (κ) | 0 | 0 | 0 |
| | Kir (λ) | 0 | 0 | 0 |
| Casts (renal tubules) | | | | |
| | Biv | 0 | 0 | ++ |
| | Cag (κ) | +++ | ++ | +++ |
| | Cle (λ) | ++ | 0 | 0 |
| | Dun (λ) | + | + | ++ |
| | Dru (κ) | ++ | + | ++ |
| | Edm (κ) | + | + | ++ |
| | Hol (κ) | + | 0 | 0 |
| | Lev (λ) | 0 | 0 | ++ |
| | Loc (λ) | 0 | 0 | 0 |
| | McC (κ) | ++ | + | ++ |
| | Mora (λ) | ++ | 0 | ++ |
| | Pat (κ) | + | 0 | + |
| | Pri (κ) | ++ | + | ++ |
| | Pug (λ) | ++ | 0 | ++ |
| | Rhy (κ) | + | 0 | + |
| | Scu (κ) | 0 | + | 0 |
| | Wat (κ) | 0 | 0 | + |
| | Wild (κ) | ++ | + | +++ |
| | Wilc (λ) | ++ | ++ | + |
| | Wit (λ) | + | 0 | + |
| Precipitates (basement membrane) | | | | |
| | Burn (κ) | ++ | 0 | 0 |
| | Cox (κ) | 0 | 0 | 0 |
| | Eve (λ) | +++ | ++ | ++ |

TABLE 1-continued

Correlation of *in vivo* pathology with *in vitro* aggregation of Bence Jones Proteins.

| Pathology Observed | Protein[1] Type | Aggregation Scores[2] | | |
|---|---|---|---|---|
| | | P[3] | Acetate[3] | Urea[3] |
| Crystals (renal tubules) | Han (κ) | ++ | + | + |
| | Kel (κ) | + | 0 | + |
| | Mon (κ) | 0 | ++ | ++ |
| Amyloid fibrils | Sho (λ) | 0 | 0 | ++ |
| | Wms (κ) | +++ | +++ | + |
| | Cro (κ) | + | 0 | + |
| | Doy (λ) | ++ | 0 | +++ |
| | Emm (λ) | ++ | 0 | 0 |
| | Mor (λ) | + | 0 | 0 |
| | She (λ) | +++ | +++ | +++ |
| | Sut (λ) | ++ | 0 | ++ |
| | Tyl (λ) | +++ | ++ | +++ |

[1]κ and λ designate two types of light chains having many sequence homologies near their carboxyl terminal domain, with characteristic variation at residue 191 and at the amino end.
Protein names are truncated versions of patient names.
[2]+ = Minimal Aggregation;
++ = Moderate Aggregation;
+++ = Heavy Aggregation.
[3]P = 50 mM sodium phosphate, 100 mM NaCl, pH 7.2;
A = 30 mM sodium acetate, 245 mM NaCl, pH 4.5;
U = 400 mM urea, 400 mM NaCl, Ph 6.5

Only one (Borf) of the non-nephrotoxic proteins aggregated under experimental conditions, but this one "false positive" categorization would be eliminated if that protein's aggregation behavior is compared to more-easily aggregated protein species, thereby reconciling the in vitro data with that obtained in vivo. As illustrated, the aggregation tendencies of the proteins tested vary with buffer solution used.

Buffer Detail

Three different buffer solutions are used, depending on the physiological site to be mimicked. The glomerulus is a major site of protein deposition, given that approximately 20 percent of cardiac output is filtered at the glomeruli. Glomerular capillaries have pore sizes of approximately 40 Å. As such, a compound will not pass through the glomerulus unless that compound's molecular weight is less than approximately 60,000. Glomerular filters allow all of the solutes of the blood plasma, except larger proteins and lipoproteins, to pass into the renal tubules. In the case of determining protein deposition in the glomerulus, Buffer 1 of 7.2 pH consisting of 50 mM sodium phosphate and 0.10 M NaCl is used. This buffer is isotonic with serum and represents conditions expected during transport of protein in the bloodstream and filtration in the glomerulus.

As the glomerular filtrate passes down the renal tubules, $Na^+$, $Cl-$, glucose, amino acids and water are reabsorbed into the blood, which passes through fine capillaries surrounding the renal tubules. Therefore, the glomerular filtrate becomes more concentrated as it proceeds down the renal tubules and toward the distal tubules. Buffer 2 is employed to mimic conditions of the microenvironment of the distal tubule. This buffer consists of 50 mM sodium phosphate, 0.4 M NaCl, and 0.4 M urea and has a pH of 6.5. The salt concentration of Buffer 2 is at the hyperosmotic end of the normal range as would occur during partial dehydration. Partial dehydration significantly exacerbates renal pathology associated with Bence Jones proteins.

With acidification as a contributing factor to the nephrotoxicity of Bence Jones proteins, a relatively acidic (4.5 pH) buffer is also utilized. This acidic buffer, Buffer 3, consists of 30 mM sodium acetate and 0.245 M NaCl. Buffer 3 provides the low pH conditions found in the renal proximal tubule, which is the site of light-chain catabolism as well as urine acidification.

Elution Profiles of Free and Aggregated Bence Jones Proteins

The molecular form of each Bence Jones protein studied was determined by SDS polyacrylamide gel electrophoresis and gel filtration (data not shown). Each sample was free of high molecular weight contaminants that would account for aggregates observed by size exclusion chromatography. Generally, λ-light chains are found predominantly as covalent dimers and κ-chains as mixtures of covalent dimers, free light-chain monomers, and as fragments corresponding in $M_r$ to a single light-chain domain. Over the past three decades, the primary structures of hundreds of light chains (complete and partial) from human and other sources, have been determined, aligned and archived. Kabat, E. A. et al. (1987) *Sequences of Proteins of Immunological Interest*, U.S. DHHS, National Institutes of Health, Bethesda, Md.

The inventor has found that light-chain dimers ($M_r \approx 45,000$) and monomers ($M_r \approx 22,500$) elute at characteristic positions on the chromatographs generated by the invented method, specifically, these entities elute at the $V_e/V_t$ positions of 0.6 and 0.7, respectively. These positions are designated with vertical lines on FIGS. 2–4.

For this particular chromatography configuration, material eluting at a $V_e/V_t$ position less than 0.6 would indicate light chain aggregation. As can be noted in FIGS. 2A, 2B, & 2C a nontoxic protein (Len), eluted well within the expected elution positions for relatively small macromolecules.

FIGS. 3A, 3B & 3C also depict an elution curve characteristic of a toxic protein (She) wherein said protein elutes in a continuum beginning at a $V_e/V_t$ position of 0.4.

FIGS. 4A, 4B, & 4C also depict an elution curve for a cast-forming Bench Jones protein (Cag). Cag exhibited high-order aggregation in PBS and the denaturing urea buffer, as evidenced by its elution as a continuum ranging from position 0.6 (dimer) to position 3.5 (excluded volume). Under acidic conditions, protein Cag has a predominantly bimodal elution pattern with a principle elution peak at $V_e/V_t=0.55$, corresponding to the position of a light chain tetramer of $M_r \approx 90,000$.

FIG. 5 depicts elution curves for three proteins, one of which is nontoxic (Len), another that is borderline toxic (Cag) and the third protein (She), discussed supra in FIG. 3, that is relatively very toxic. Cag was monitored at 4.8 mg/ml in Acetate buffer at 4.5 pH, while Len and She was monitored at 2.0 mg/ml in PBS at 7.2 pH. All three proteins elute at their respective $V_e/V_t$ ratios, corresponding to the sizes of the macromolecules observed by the inventor to elute at these positions.

While the invention has been described with reference to details of the illustrated embodiment, these details are not intended to limit the scope of the invention as defined in the appended claims.

The embodiment of the invention in which an exclusive property or privilege is claimed is defined as follows:

1. A method for screening for disease by detecting pathological light chain proteins in a patient, comprising:
   obtaining body fluid from the patient, said body fluid containing the pathological light chain proteins;
   pretreating the body fluid so as to facilitate in vitro aggregation of the pathological light chain proteins;

subjecting the pretreated body fluid to non-silica based HPLC chromatography to aggregate the light chain proteins;

eluting the aggregated light chain proteins as an excluded fluid within 30 to 35 minutes; and analyzing the excluded fluid to screen for light chain proteins having a predetermined molecular weight in order to diagnose protein-aggregation-related disease in the patient.

2. The method as recited in claim 1 wherein the body fluid is selected from the group consisting of urine, blood, serum, and combinations thereof.

3. The method as recited in claim 1 wherein the step of subjecting the pretreated body fluid to non-silica HPLC chromatography further comprises:

saturating a size exclusion column with buffer solution at a rate of between approximately 0.01 ml/min and 2 ml/min; and injecting the pretreated body fluid into the column in a volume ranging from between approximately 1 $\mu$l to 50 $\mu$l.

4. The method as recited in claim 1 wherein the predetermined molecular weight is between approximately 60,000 and 200,000 daltons.

5. The method as recited in claim 1 wherein the step of analyzing the excluded fluid further comprises measuring the radiation absorbance of the excluded fluid at a predetermined wavelength to produce a chromatogram elution profile;

normalizing the chromatogram elution profile such that the integrated area under the elution profile is equal to one; and comparing the normalized chromatogram elution profile with an elution profile database of known pathologic proteins.

6. The method as recited in claim 1 wherein a predetermined protein to buffer concentration is selected from a range of between approximately 0.01 mg/ml and 50 mg/ml.

7. The method as recited in claim 1 wherein the step of pretreating the body fluid further comprises:

purifying the fluid to remove contaminants having a molecular weight greater than the pathological light chain proteins from the fluid containing the pathological light chain proteins; and mixing the now purified fluid with a predetermined buffer solution in predetermined concentrations of pathological light chain proteins to buffer solution so as to mimic physiological conditions of an organ and to aggregate the light chain proteins.

8. The method as recited in claim 7 wherein the predetermined concentrations range from approximately 0.01 mg/ml to 50 mg/ml of pathological light chain proteins to buffer solution.

9. The method as recited in claim 7 wherein the predetermined buffer solution is selected from the group consisting of buffer 1 having a pH of approximately 7.2 and which consists of 50 mM sodium phosphate and 0.10 M NaCl, buffer 2 having a pH of 6.5 and which consists of 50 mM sodium phosphate, 0.4 M NaCl and 0.4 M Urea, buffer 3 having a pH of 4.5 and which consists of 30 mM sodium acetate and 0.245 M NaCl, and combinations thereof.

10. A method for detecting disease by screening for nephrotoxic antibody light chains in a patient comprising:

obtaining urine from the patient;

isolating protein from the urine;

pretreating the isolated protein by mixing the isolated protein with a predetermined buffer solution in a predetermined protein to buffer concentration so as to mimic physiological conditions of the kidneys so as to facilitate aggregation of the light chains;

aggregating the light chains on a non-silica based HPLC chromatography column;

eluting the aggregated light chains so as to create an excluded fluid within 30–35 minutes;

subjecting the excluded fluid to ultra violet radiation to observe radiation absorption levels;

normalizing the protein's absorption spectra; and comparing the normalized absorption spectra to a absorption spectra of nephrotoxic proteins in order to screen for protein-aggregation-related disease as a complication of multiple myeloma.

11. The method as recited in claim 10 wherein the predetermined buffer solution is selected from the group consisting of buffer 1 having a pH of approximately 7.2 and which consists of 50 mM sodium phosphate and 0.10 M NaCl, buffer 2 having a pH of 6.4 and which consists of 50 mM sodium phosphate, 0.4 M NaCl and 0.4 M Urea, buffer 3 having a pH of 4.5 and which consists of 30 mM sodium acetate and 0.245 M NaCl, and combinations thereof.

12. The method as recited in claim 10 wherein the ultraviolet radiation has a wavelength of 214 nm or 280 nm.

13. The method as recited in claim 10 wherein the elution profile of nephrotoxic proteins depict relatively high absorption at a $V_e/V_t$ position of less than 0.6 compared to the elution profile of nonnephrotoxic protein of a $V_e/V_t$ position of less than 0.6.

14. The method as recited in claim 10 wherein the aggregated nephrotoxic antibody light chains have a molecular weight of at least 60,000 daltons.

15. The method as recited in claim 10 wherein the buffer has a pH of approximately 7.2 and consists of 50 mM sodium phosphate and 0.10 M NaCl, so as to mimic conditions expected during transport of the protein in the bloodstream and filtration in the glomerulus.

16. The method as recited in claim 10 wherein the buffer has a pH of 6.4 and consists of 50 mM sodium phosphate, 0.4 M NaCl and 0.4 M Urea, so as to mimic conditions of the microenvironment of the distal tube.

17. The method as recited in claim 10 wherein the buffer has a pH of 4.5 and consists of 30 mM sodium acetate and 0.245 M NaCl, so as to mimic conditions of the renal proximal tubule.

18. A method for detecting protein deposition disease in a person by the in vitro assembling of molecules found in the person's body fluid to create pathological macromolecules, comprising:

extracting the body fluid from the patient;

pretreating the body fluid by mixing the body fluid with a buffer solution to assemble molecules into pathological light chain proteins;

subjecting the pretreated body fluid to non-silica based HPLC chromatography to create an excluded fluid; and analyzing the excluded fluid to detect pathological light chain proteins having a predetermined molecular weight.

19. The method as recited in claim 18 wherein the body fluid is selected from the group consisting of urine, blood, serum, and combinations thereof.

20. The method as recited in claim 18 wherein the predetermined molecular weight is between approximately 60,000 and 200,000 daltons.

* * * * *